US012622617B2

(12) United States Patent (10) Patent No.: US 12,622,617 B2
Lee et al. (45) Date of Patent: May 12, 2026

(54) AUDIO AND VISUAL INPUT ANALYSIS

(71) Applicant: Micron Technology, Inc., Boise, ID (US)

(72) Inventors: Yunju Lee, Boise, ID (US); Sue-Fern Ng, Boise, ID (US); Bhumika Chhabra, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 1170 days.

(21) Appl. No.: 17/564,647

(22) Filed: Dec. 29, 2021

(65) Prior Publication Data

US 2023/0200696 A1    Jun. 29, 2023

(51) Int. Cl.
| *A61B 5/16* | (2006.01) |
| *A61B 5/00* | (2006.01) |
| *G06N 20/00* | (2019.01) |
| *G16H 20/30* | (2018.01) |
| *G16H 20/70* | (2018.01) |

(52) U.S. Cl.
CPC ............ *A61B 5/165* (2013.01); *A61B 5/4803* (2013.01); *G06N 20/00* (2019.01); *G16H 20/30* (2018.01); *G16H 20/70* (2018.01)

(58) Field of Classification Search
CPC .............................................. A61B 5/165–167
See application file for complete search history.

(56) References Cited

U.S. PATENT DOCUMENTS

| 9,183,632 B2 | 11/2015 | Higa | |
| 9,715,622 B2 | 7/2017 | Rao | |
| 10,043,099 B2 | 8/2018 | Wang | |
| 2010/0221687 A1 | 9/2010 | Forbes | |
| 2014/0297316 A1* | 10/2014 | Noordvyk | .............. G16H 10/20 |
| | | | 705/3 |
| 2017/0105662 A1 | 4/2017 | Silawan | |
| 2018/0075198 A1* | 3/2018 | Hwang | ................. G16H 20/00 |
| 2023/0326089 A1* | 10/2023 | Kim | ........................ A61B 5/165 |
| 2023/0346280 A1* | 11/2023 | Kim | ........................ A61B 5/165 |

FOREIGN PATENT DOCUMENTS

| KR | 101772987 B1 * | 8/2017 | ........... A61B 5/0002 |
| KR | 20180013777 A * | 2/2018 | .............. A61B 5/165 |

* cited by examiner

*Primary Examiner* — Thaddeus B Cox
(74) *Attorney, Agent, or Firm* — Brooks, Cameron & Huebsch, PLLC

(57) ABSTRACT
Methods, devices, and systems associated with audio and visual input analysis are described. A method can include recording audio during production of artwork using a microphone, storing the audio recording in tiered memory, generating an image of the artwork using an image sensor, storing the image of the artwork in the tiered memory, receiving a reference library including a number of audio recordings and a number of images of artwork, comparing the image of the artwork to the number of images of artwork and the audio recording to the number of audio recordings, and providing an output in response to at least one of: the image of the artwork matching one of the number of images of artwork or the audio recording matching one of the number of audio recordings.

13 Claims, 4 Drawing Sheets

340 — PROVIDE INSTRUCTIONS AND ASK QUESTIONS

342 — GENERATE IMAGE AND RECORD AUDIO

344 — PROVIDE ADDITIONAL INPUT INFORMATION

346 — COMPARE DATA TO REFERENCE LIBRARY

348 — DATA MATCHES?

350 — PROVIDE OUTPUT

352 — PERMISSION TO TRANSMIT DATA?

354 — TRANSMIT DATA TO CONTACT

356 — PROVIDING CONTACT INFO

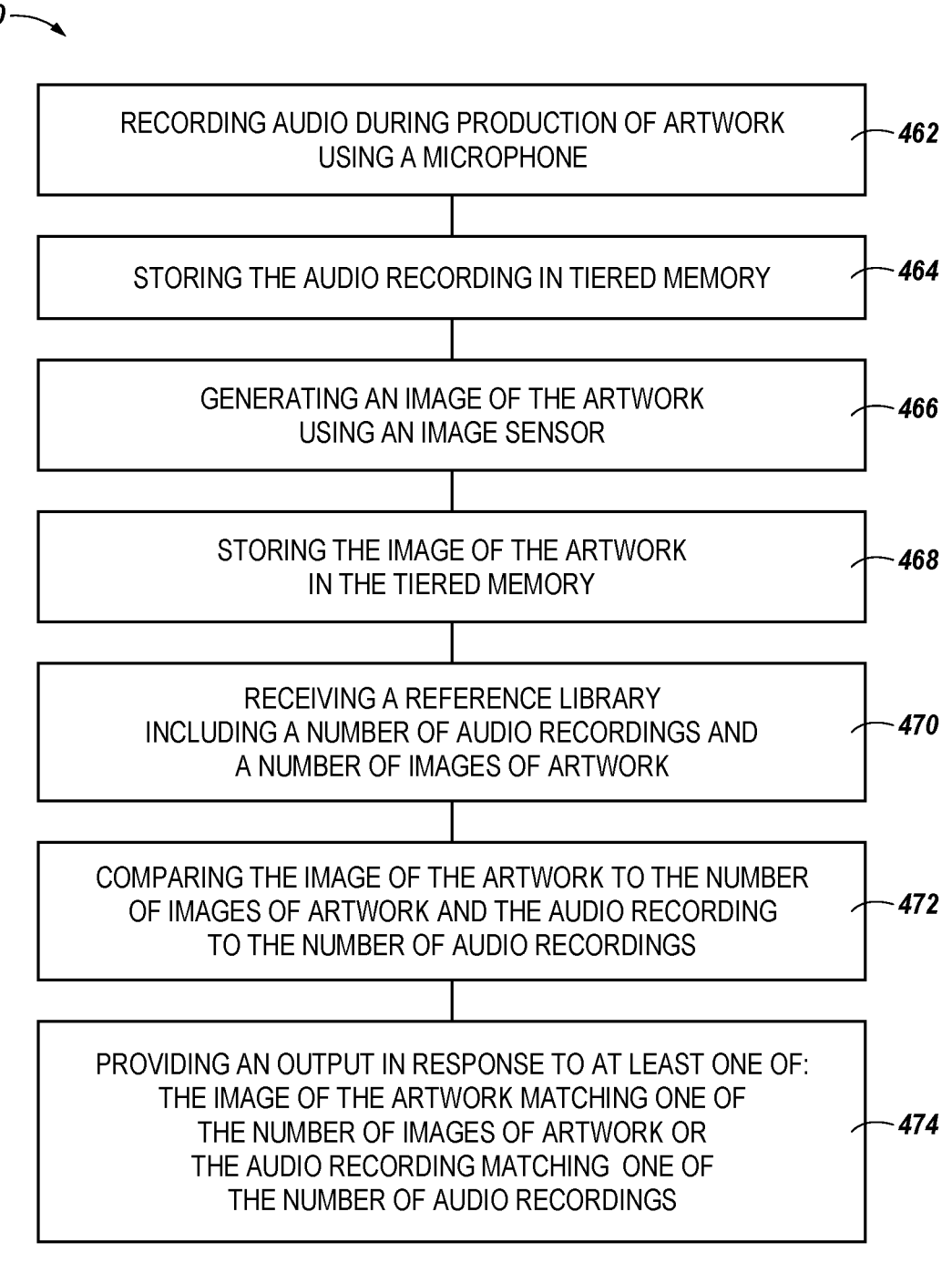

460

RECORDING AUDIO DURING PRODUCTION OF ARTWORK
USING A MICROPHONE — 462

STORING THE AUDIO RECORDING IN TIERED MEMORY — 464

GENERATING AN IMAGE OF THE ARTWORK
USING AN IMAGE SENSOR — 466

STORING THE IMAGE OF THE ARTWORK
IN THE TIERED MEMORY — 468

RECEIVING A REFERENCE LIBRARY
INCLUDING A NUMBER OF AUDIO RECORDINGS AND
A NUMBER OF IMAGES OF ARTWORK — 470

COMPARING THE IMAGE OF THE ARTWORK TO THE NUMBER
OF IMAGES OF ARTWORK AND THE AUDIO RECORDING
TO THE NUMBER OF AUDIO RECORDINGS — 472

PROVIDING AN OUTPUT IN RESPONSE TO AT LEAST ONE OF:
THE IMAGE OF THE ARTWORK MATCHING ONE OF
THE NUMBER OF IMAGES OF ARTWORK OR
THE AUDIO RECORDING MATCHING ONE OF
THE NUMBER OF AUDIO RECORDINGS — 474

*FIG. 4*

AUDIO AND VISUAL INPUT ANALYSIS

TECHNICAL FIELD

The present disclosure relates generally to apparatuses, systems, and methods associated with audio and visual input analysis.

BACKGROUND

A computing device can be a smartphone, a wearable device, a tablet, a laptop, a desktop computer, or a smart assistant device, for example. The computing device can receive and/or transmit data and can include or be coupled to one or more memory devices. Memory devices are typically provided as internal, semiconductor, integrated circuits in computers or other electronic systems. There are many different types of memory including volatile and non-volatile memory. Volatile memory can require power to maintain its data (e.g., host data, error data, etc.) and includes random access memory (RAM), dynamic random-access memory (DRAM), static random-access memory (SRAM), synchronous dynamic random-access memory (SDRAM), and thyristor random access memory (TRAM), among others. Non-volatile memory can provide persistent data by retaining stored data when not powered and can include NAND flash memory, NOR flash memory, and resistance variable memory such as phase change random access memory (PCRAM), resistive random-access memory (RRAM), and magnetoresistive random access memory (MRAM), such as spin torque transfer random access memory (STT RAM), among others.

BRIEF DESCRIPTION OF THE DRAWINGS

FIG. 4 is a flow diagram of a method for audio and visual input analysis in accordance with a number of embodiments of the present disclosure.

DETAILED DESCRIPTION

Figure 1:
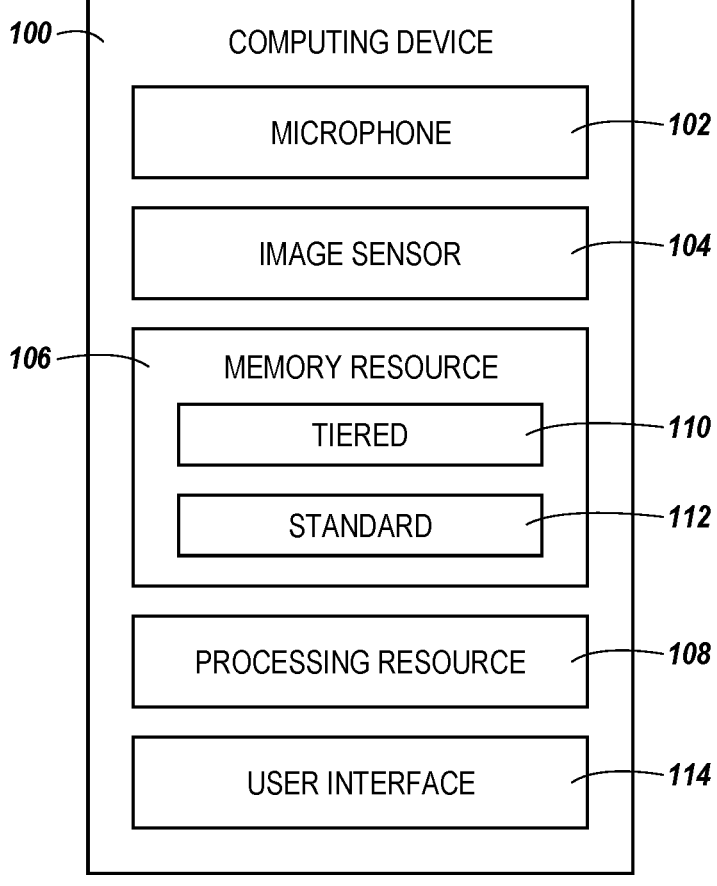
FIG. 1 illustrates an example of a computing device for audio and visual input analysis in accordance with a number of embodiments of the present disclosure.

The present disclosure includes apparatuses, systems, and methods related to recording audio during production of artwork using a microphone, storing the audio recording in tiered memory, generating an image of the artwork using an image sensor, storing the image of the artwork in the tiered memory, receiving a reference library including a number of audio recordings and a number of images of artwork, comparing the image of the artwork to the number of images of artwork and the audio recording to the number of audio recordings, and providing an output in response to the image of the artwork matching one of the number of images of artwork and/or the audio recording matching one of the number of audio recordings.

Diagnosing mental and/or behavioral issues, disorders, and/or diseases are normally done in person during a pre-scheduled appointment with a healthcare provider. A patient may not be displaying signs or symptoms during a pre-scheduled appointment which could prevent the patient from getting a diagnosis and/or proper medications or tools to cope with their disorder or disease. This can inconvenience or endanger the patient. Embodiments of the present disclosure can enable detection of mental and/or behavioral issues, disorders, and/or diseases and provide assistance in real-time.

Often data including signs and symptoms over time are not available to a healthcare provider for diagnosing a patient or gauging progress of the patient. Instead, healthcare providers rely on the patient and caretaker to convey symptoms based on their memory and knowledge, which may be limited, incomplete, and/or over a short period of time. Providing audio and visual inputs over time can convey a more comprehensive and detailed picture of the patient's symptoms and progression for the healthcare provider, which can lead to a more accurate diagnosis and a more precise treatment.

As used herein, "a number of" something can refer to one or more of such things. A "plurality" of something intends two or more. The figures herein follow a numbering convention in which the first digit or digits correspond to the drawing figure number and the remaining digits identify an element or component in the drawing. Similar elements or components between different figures may be identified by the use of similar digits. For example, reference numeral 106 may reference element "6" in FIG. 1, and a similar element may be referenced as 206 in FIG. 2. In some instances, a plurality of similar, but functionally and/or structurally distinguishable, elements or components in the same figure or in different figures may be referenced sequentially with the same element number. As will be appreciated, elements shown in the various embodiments herein can be added, exchanged, and/or eliminated so as to provide a number of additional embodiments of the present disclosure. In addition, the proportion and the relative scale of the elements provided in the figures are intended to illustrate various embodiments of the present disclosure and are not to be used in a limiting sense.

FIG. 1 illustrates an example of a computing device 100 for audio and visual input analysis in accordance with a number of embodiments of the present disclosure. The computing device 100 can be, but is not limited to, a smartphone, a wearable device, a tablet, a laptop, a desktop computer, a smart assistant device, or any combination thereof. The computing device 100 can further include a microphone 102, an image sensor 104 (e.g., camera), a memory resource (e.g., memory) 106, a processing resource (e.g., processor) 108, and/or a user interface 114.

The memory 106 can include volatile and/or non-volatile memory, for instance, DRAM and/or NAND. The memory 106 can be coupled to the processor 108 and can include tiered memory 110 and/or standard memory 112. The memory 106 can be any type of storage medium that can be accessed by the processor 108 to perform various examples of the present disclosure. For example, the memory 106 can be a non-transitory computer readable medium having computer readable instructions (e.g., computer program instructions) stored thereon that are executable by the processor 108 to record audio during production of artwork using the microphone 102, store the audio recording in the tiered memory 110, generate an image of the artwork using the image sensor 104, store the image of the artwork in the tiered memory 110, receive a reference library including a number of audio recordings and a number of images of artwork, compare the image of the artwork to the number of images of artwork and the audio recording to the number of audio recordings, and provide an output in response to at least one of: the image of the artwork matching one of the number of images of artwork or the audio recording matching one of the number of audio recordings.

The memory 106 can include the tiered memory 110 for content that requires more memory and processing load and the standard memory 112 for content that requires less memory and processing load. The processor 108 can store the audio recording, the image of the artwork, and/or the reference library in tiered memory 110 for performing the comparison operation more efficiently. The reference library can be accessed through an application on and/or an operating system of the computing device 100. Performing the comparison operation on the memory device 100 and storing the audio recording and/or the image of the artwork in the memory 106 of the computing device 100 can keep the patient's private information secure.

In a number of embodiments, the computing device 100 can generate the user interface 114. The user interface 114 can be a graphical user interface (GUI) that can provide and/or receive information to and/or from a user of the computing device 100. The user interface 114 can be shown on a display of the computing device 100. In some examples, the user interface 114 can provide instructions to produce the artwork. For example, the user interface 114 may instruct the user to draw a tree. The user interface 114 may also provide a number of questions for the user to answer while producing the artwork. In some examples, the user interface 114 can receive answers to the number of questions. For example, a patient and/or caretaker may provide answers or additional information using the user interface 114.

If the comparison of the image of the artwork to the number of images of artwork and/or the comparison of the audio recording to the number of audio recordings result in a match, the user interface 114 may display the output including a diagnosis, an exercise, advice, and/or contact information. The output could be a calming game, music, and/or a suggestion to provide encouragement to the patient, for example.

If the comparison of the image of the artwork to the number of images of artwork and/or the comparison of the audio recording to the number of audio recordings does not result in a match, the user interface 114 may display a request for permission to transmit the image of the artwork and/or the audio recording. The user may ignore the request or make a selection using the user interface 114. If the user selects to transmit the image of the artwork and/or the audio recording, the processor 108 can transmit the image of the artwork and/or the audio recording to a particular contact. The particular contact can be a doctor, a psychologist, a social worker, and/or a support group identified based on the artwork and/or the audio recording, for example.

The computing device 100 can receive correspondence from the particular contact. The correspondence can be conveyed to the user via the user interface 114. In some examples, the correspondence can include a diagnosis, an exercise, advice, and/or contact information.

Figure 2:
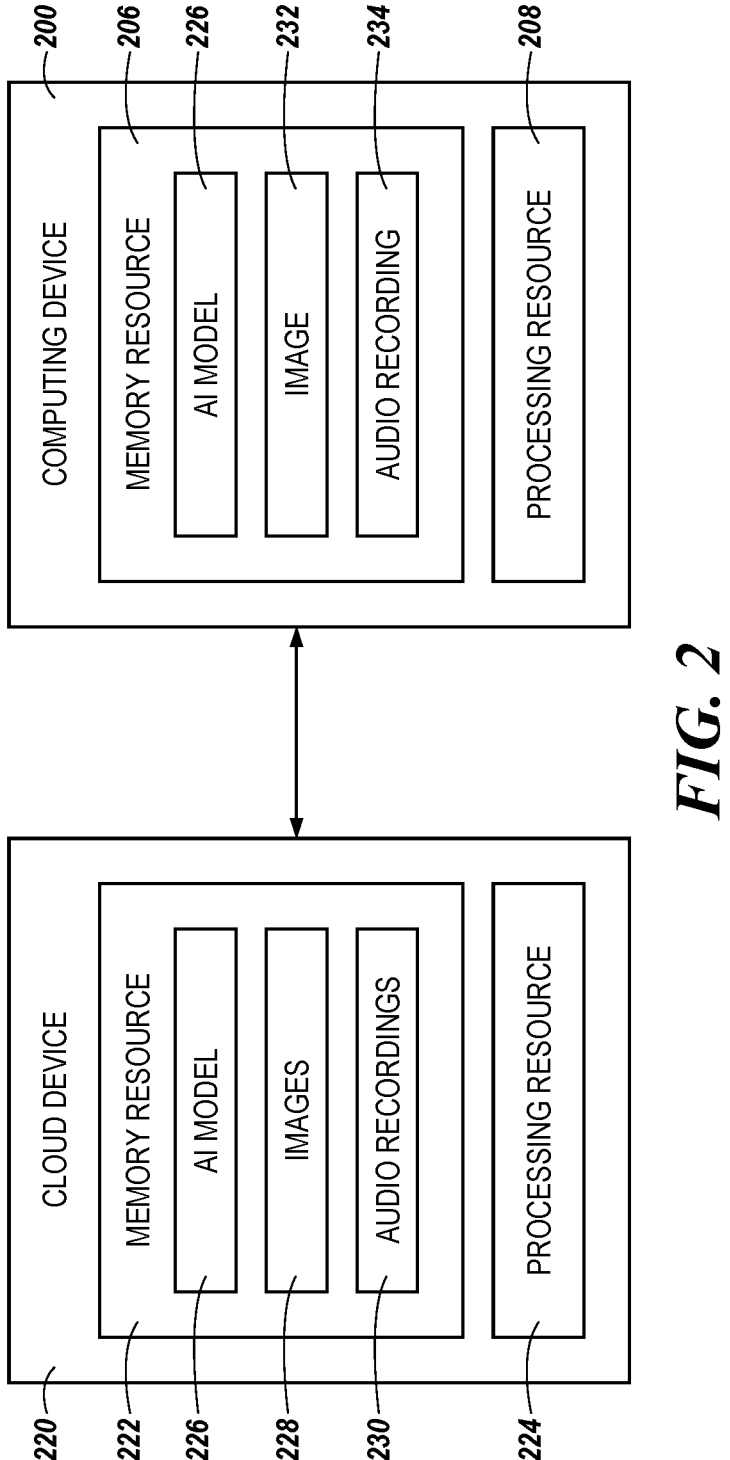
FIG. 2 illustrates an example of a system for audio and visual input analysis in accordance with a number of embodiments of the present disclosure.

FIG. 2 illustrates an example of a system for audio and visual input analysis in accordance with a number of embodiments of the present disclosure. The system illustrated in FIG. 2 can include a cloud device 220 and a computing device 200.

The cloud device 220 can be, but is not limited to, a cloud computing device, a server, or any combination thereof located remotely from the computing device 200. The cloud device 220 can include a memory resource (e.g., memory) 222 and a processing resource (e.g., processor) 224. The memory 222 can include volatile and/or non-volatile memory. The memory 222 can be coupled to the processor 224 and can store an artificial intelligence (AI) model 226, a number of images of artwork 228, and/or a number of audio recordings 230. The number of images of artwork 228 and/or the number of audio recordings 230 can be included in a reference library, as previously discussed in connection with FIG. 1. The memory 222 can be any type of storage medium that can be accessed by the processor 224 to perform various examples of the present disclosure. For example, the memory 222 can be a non-transitory computer readable medium having computer readable instructions stored thereon that are executable by the processor 224 to train the AI model 226 with the number of images of artwork 228 and the number of audio recordings 230 corresponding to each of the number of images of artwork 228 and transmit the AI model 226.

The computing device 200 can receive the AI model 226 from the cloud device 220. The computing device 200 and/or the cloud device 220 can communicate (e.g., transmit and/or receive data) via a network relationship. Examples of such a network relationship can include Bluetooth, AirDrop, a peer-to-peer Wi-Fi network, a cellular network, a distributed computing environment (e.g., a cloud computing environment), a wide area network (WAN) such as the Internet, a local area network (LAN), a personal area network (PAN), a campus area network (CAN), or metropolitan area network (MAN), among other types of network relationships.

The computing device 200 can correspond to computing device 100 in FIG. 1. The computing device 200 can include hardware, software, and/or firmware that is configured to perform operations (e.g., logic operations, among other operations) associated with AI operations using the AI model 226. In some examples, the AI model 226 can be trained on and/or updated on the computing device 200. Data from a user of the computing device 200 including the image of the artwork 232 and/or the audio recording 234 or sample data including the number of images of artwork 228 and/or the number of audio recordings 230 can be used to train and/or update the AI model 226.

If the AI model 226 is trained on and/or updated external to the computing device 200, for example on the cloud device 220. The data from a user of the computing device 200 including the image of the artwork 232 and/or the audio recording 234 can be transmitted from the computing device 200 to the cloud device 220. In a number of embodiments, the computing device 200 can transform data representing the image of the artwork 232 and/or the audio recording 234 by removing personal data from the image of the artwork 232 and/or the audio recording 234 prior to sending the image of the artwork 232 and/or the audio recording 234 to the cloud device 220. For example, a signature on the image of the artwork 232 and/or a name mentioned in the audio recording 234 can be covered and/or removed.

The cloud device 220 can receive the transformed and/or untransformed data representing the image of the artwork 232 and/or the audio recording 234 and use the image of the artwork 232 and/or the audio recording 234 along with the number of images of artwork 228 and/or the number of audio recordings 230 to train and/or update the AI model 226. In a number of embodiments, the number of images of artwork 228 and/or the number of audio recordings 230 can be received at the cloud device 220 from an authorized user. An authorized user can be a doctor, a psychologist, a social worker, and/or an administrator of the reference library and/or the AI model 226, for example. The authorized user can ensure that only legitimate data is being added to the reference library and/or training the AI model 226.

The computing device 200 can receive the trained and/or updated AI model 226 from the cloud device 220. The AI model 226 can be accessed through an application on and/or an operating system of the computing device 200. The computing device 200 can perform an AI operation on the image of the artwork 232 and/or the audio recording 234 using the AI model 226. In a number of embodiments, the processor 208 can input additional data into the AI model 226. For example, the processor 208 can determine a current time, day, date, and/or location via the operating system of the computing device 200, applications of the computing device 200 (e.g., a calendar application), and/or a geographic position system (GPS) of the computing device 200. A timestamp including the current time, day, and/or date and/or the location can be inputted into the AI model 226. A patient and/or caretaker may provide additional data. The additional data can include the mood and/or behaviors of the patient, for example. The processor 208 can input the additional data.

In some examples, the computing device 200 can output a result of the AI operation 226. The output can be displayed via a user interface (e.g., user interface 114 in FIG. 1) of the computing device 200. The output can be a diagnosis, an exercise, advice, and/or contact information.

Figure 3:
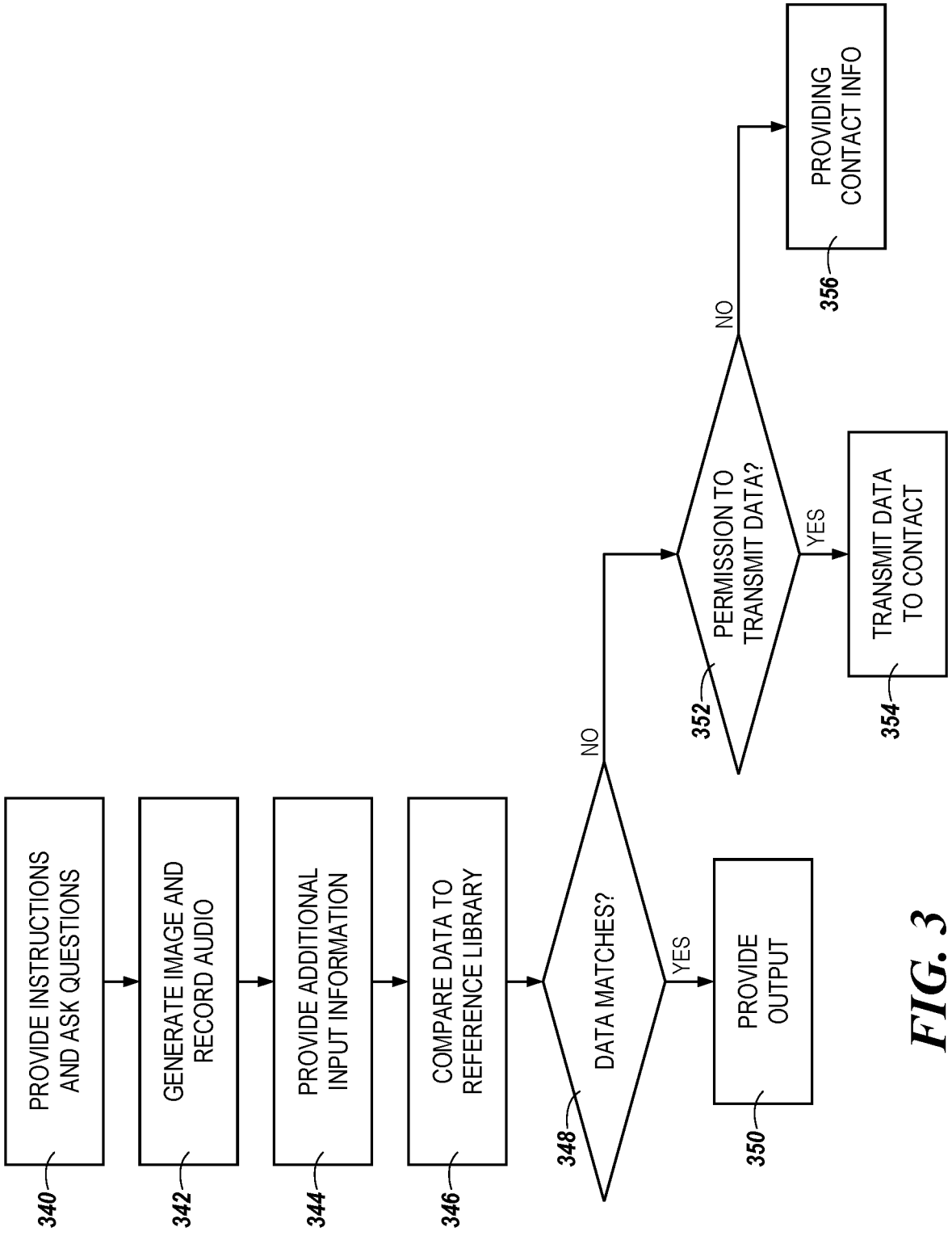
FIG. 3 illustrates an example of a flow diagram for audio and visual input analysis in accordance with a number of embodiments of the present disclosure.

FIG. 3 illustrates an example of a flow diagram for audio and visual input analysis in accordance with a number of embodiments of the present disclosure. A user interface (e.g. user interface 114 in FIG. 1) of a computing device (e.g., computing device 100 in FIG. 1 and/or computing device 200 in FIG. 2) can provide instructions and/or ask questions at block 340. The instructions can include a request to create a particular artwork. While the patient is creating the artwork, the computing device can ask questions. The questions can elicit the patient's name, favorite food, and/or favorite pet, for example.

An image sensor (e.g., image sensor 104 in FIG. 1) of the computing device can generate an image of the artwork (e.g., image of the artwork 232 in FIG. 2) and a microphone (e.g., microphone 102 in FIG. 1) can record audio (e.g., audio recording 234 in FIG. 2) while the artwork is being created at block 342. The artistic choices made and/or the tone of the patient's voice can reflect the patient's mindset, temperament, and/or stress level, for example.

A patient and/or a caretaker can provide additional input information at block 344. For example, the patient and/or caretaker can provide previous moods and/or behaviors of the patient and/or provide possible triggers for the patient's current state. The additional input information can be received by the computing device via the user interface of the computing device and/or via the microphone of the computing device.

At block 346, the data representing the image of the artwork, the audio recording, and/or the additional input information can be compared to data in a reference library. The reference library can include a number of audio recordings and/or a number of images of artwork each associated with a mood, mental and/or behavioral issue, disorder, and/or disease, exercises, contacts, and/or advice. For example, the reference library can include audio recordings and/or images of artwork from patients with oppositional defiant disorder (ODD), obsessive-compulsive disorder (OCD), attention deficit hyperactivity disorder (ADHD), and/or Bipolar disorder. In some examples, the reference library may include previous audio recordings and/or images of artwork from the patient for assisting and/or diagnosing other patients and/or for measuring progress of the patient over time.

If the computing device determines the data matches at block 348, the computing device can provide an output at block 350. A match can be determined between the image of the artwork and one of the number of images of artwork if a number of characteristics present in the image of the artwork are found in one of the number of images of artwork in the reference library. Characteristics could include, but are not limited to, line thicknesses, use of colors, choice of perspective, use of light, and/or use of shadow. If the image of the artwork includes a lot of bright colors, the image of the artwork can match with one of the number of images of artwork that also includes bright colors. Accordingly, the computing device can provide an output at block 350 including the mood, mental and/or behavioral issue, disorder, and/or disease, exercises, contacts, and/or advice associated with the one of the number of images of artwork that matched with the image of the artwork created by the patient.

A match can be determined between the audio recording and one of the number of audio recordings if a number of characteristics present in the audio recording are found in one of the number of audio recordings in the reference library. Characteristics could include, but are not limited to, volume, rate, pitch, fluency, articulation, and/or tone. If the patient is loud on the audio recording, the audio recording can match with one of the number of audio recordings that also includes a loud patient. Accordingly, the computing device can provide an output at block 350 including the mood, mental and/or behavioral issue, disorder, and/or disease, exercises, contacts, and/or advice associated with the one of the number of audio recordings that matched with the audio recording created by the patient.

If the computing device determines the data does not match at block 348, the computing device can request permission to transmit the data representing the image of the artwork, the audio recording, and/or the additional input information at block 352. The permission can be received by the computing device via the user interface of the computing device and/or via the microphone of the computing device.

If the computing device receives permission, the computing device will transmit the data to a contact at block 354. The contact can be a doctor, psychiatrist, psychologist, social worker, and/or support group. The computing device can transform data representing the image of the artwork and/or the audio recording by removing personal data from the image of the artwork and/or the audio recording prior to sending the image of the artwork and/or the audio recording to the contact. This can protect a patient's identity and/or personal information from being manipulated and/or exposed.

If the computing device does not receive permission, the computing will provide contact information at block 356. The contact information can be for a doctor, psychiatrist, psychologist, social worker, and/or support group. A specific contact can be determined based on the image of the artwork and/or the audio recording. For example, if the image of the artwork and/or the audio recording includes characteristics associated with depression, the computing device can provide contact information for a psychologist near the patient if location data was provided.

FIG. 4 is a flow diagram of a method 460 for audio and visual input analysis in accordance with a number of embodiments of the present disclosure. At block 462, the method 460 can include recording audio during production of artwork using a microphone. The audio recording can correspond to audio recording 234 in FIG. 2.

At block 464, the method 460 can include storing the audio recording in tiered memory. The tiered memory can correspond to tiered memory 110 in FIG. 1. The tiered memory can provide more memory and processing load for performing operations on the audio recording.

At block 466, the method 460 can include generating an image of the artwork using an image sensor. The image sensor can be a camera. The image of the artwork can correspond to the image of the artwork 232 in FIG. 2.

At block 468, the method 460 can include storing the image of the artwork in the tiered memory. The tiered memory can provide more memory and processing load for performing operations on the image of the artwork.

At block 470, the method 460 can include receiving a reference library including a number of audio recordings and a number of images of artwork. The reference library can include a number of audio recordings and/or a number of images of artwork each associated with a mood, mental and/or behavioral issue, disorder, and/or disease, exercises, contacts, and/or advice.

At block 472, the method 460 can include comparing the image of the artwork to the number of images of artwork and the audio recording to the number of audio recordings. Characteristics of the image of artwork can be compared to characteristics of each of the number of images of artwork. Characteristics of artwork can include, but are not limited to, line thicknesses, use of colors, choice of perspective, use of light, and/or use of shadow. Characteristics of the audio recording can be compared to characteristics of each of the number of audio recordings. Characteristics of audio recording can include, but are not limited to, volume, rate, pitch, fluency, articulation, and/or tone.

At block 474, the method 460 can include providing an output in response to at least one of: the image of the artwork matching one of the number of images of artwork or the audio recording matching one of the number of audio recordings. The output can include the mood, mental and/or behavioral issue, disorder, and/or disease, exercises, contacts, and/or advice associated with the one of the number of audio recordings that matched with the audio recording created by the patient.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and methods are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method, comprising:
recording audio during production of artwork using a microphone;
storing the audio recording in tiered memory;
generating an image of the artwork using an image sensor;
storing the image of the artwork in the tiered memory;
receiving a reference library including a number of audio recordings and a number of images of artwork;
comparing the image of the artwork to the number of images of artwork and the audio recording to the number of audio recordings, wherein a processor is configured to store the audio recording and the image of the artwork in the tiered memory to perform the comparison more efficiently;
providing an output in response to at least one of: the image of the artwork matching one of the number of images of artwork or the audio recording matching one of the number of audio recordings; and
requesting permission, via a user interface, to transmit at least one of: the image of the artwork or the audio recording in response to at least one of: the image of the artwork being different from the number of images of artwork or the audio recording being different from the number of audio recordings.

2. The method of claim 1, further comprising providing instructions to produce the artwork via the user interface.

3. The method of claim 1, further comprising providing a number of questions via the user interface.

4. The method of claim 3, further comprising receiving answers to the number of questions via the user interface.

5. The method of claim 1, further comprising receiving permission, via the user interface, to transmit at least one of: the image of the artwork or the audio recording.

6. The method of claim 5, further comprising identifying a doctor, a psychologist, a psychiatrist, a social worker, or a support group based at least in part on at least one of: the image of the artwork or the audio recording in response to at least one of: the image of the artwork being different from the number of images of artwork or the audio recording being different from the number of audio recordings.

7. The method of claim 6, further comprising transmitting at least one of: the image of the artwork or the audio recording to at least one of: the doctor, the psychologist, the psychiatrist, the social worker, or the support group.

8. The method of claim 7, further comprising receiving correspondence, via the user interface, from at least one of: the doctor, the psychologist, the psychiatrist, the social worker, or the support group.

9. The method of claim 1, further comprising providing the output including at least one of: a diagnosis, an exercise, advice, or contact information via the user interface.

10. An apparatus, comprising:
a microphone configured to record audio during production of artwork;
an image sensor configured to generate an image of the artwork;
a memory resource including tiered memory; and
a processing resource configured to:
compare the image of the artwork to a number of images of artwork and the audio recording to a number of audio recordings, wherein the processor is configured to store the audio recording and the image of the artwork in the tiered memory to perform the comparison more efficiently; and request permission, via a user interface, to transmit at least one of: the image of the artwork or the audio recording in response to at least one of: the image of the artwork being different from the number of images of artwork or the audio recording being different from the number of audio recordings.

11. The apparatus of claim 10, wherein the processing resource is configured to input at least one of: a timestamp or a location into an artificial intelligence (AI) model.

12. The apparatus of claim 10, wherein the user interface is configured to receive data from a caretaker.

13. The apparatus of claim 12, wherein the processing resource is configured to:

input the data from the caretaker into an artificial intelligence (AI) model;

perform an AI operation using the AI model; and output a result of the AI operation.

* * * * *